United States Patent
Dadaglio et al.

(10) Patent No.: US 9,410,139 B2
(45) Date of Patent: Aug. 9, 2016

(54) **RECOMBINANT ADENYLATE CYCLASE TOXIN OF *BORDETELLA* INDUCES T CELL RESPONSES AGAINST TUMORAL ANTIGENS**

(75) Inventors: Gilles Dadaglio, Chatillen (FR); Claude Leclerc, Paris (FR); Daniel Ladant, Cachan (FR); Benoît Van Den Eynde, Brussels (BE); Sandra Morel, Brussels (BE); Cécile Bauche, Paris (FR)

(73) Assignees: INSTITUT PASTEUR, Paris (FR); INSTITUT NATIONAL DE LA SANTE ET DE LA RECHERCHE MEDICALE (INSERM), Paris (FR); LUDWIG INSTITUT FOR CANCER RESEARCH, New York, NY (US); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 142 days.

(21) Appl. No.: 12/232,250

(22) Filed: Sep. 12, 2008

(65) Prior Publication Data
US 2009/0117143 A1    May 7, 2009

Related U.S. Application Data

(63) Continuation of application No. 11/436,757, filed on May 19, 2006, now abandoned, which is a continuation of application No. PCT/EP2004/014086, filed on Nov. 19, 2004.

(60) Provisional application No. 60/523,632, filed on Nov. 21, 2003.

(51) Int. Cl.
| | | |
|---|---|---|
| *C12N 9/88* | (2006.01) | |
| *A61K 38/16* | (2006.01) | |
| *A61K 39/00* | (2006.01) | |
| *A61K 39/39* | (2006.01) | |
| *A61K 47/48* | (2006.01) | |

(52) U.S. Cl.
CPC ............ *C12N 9/88* (2013.01); *A61K 38/164* (2013.01); *A61K 39/0011* (2013.01); *A61K 39/39* (2013.01); *A61K 47/4833* (2013.01); *A61K 47/48261* (2013.01); *C12Y 406/01001* (2013.01); *A61K 2039/6037* (2013.01); *A61K 2039/6068* (2013.01)

(58) Field of Classification Search
None
See application file for complete search history.

(56) References Cited

U.S. PATENT DOCUMENTS

| | | |
|---|---|---|
| 5,503,829 A | 4/1996 | Ladant et al. |
| 5,679,784 A | 10/1997 | Ladant et al. |
| 5,821,122 A * | 10/1998 | Guilloux et al. ............... 435/325 |
| 5,935,580 A | 8/1999 | Ladant et al. |
| 6,500,641 B1 | 12/2002 | Chen et al. |
| 2014/0227323 A1 | 8/2014 | Dadaglio |

FOREIGN PATENT DOCUMENTS

| | | |
|---|---|---|
| EP | 1 188 446 A1 | 3/2002 |
| WO | WO-01/29220 A2 | 4/2001 |
| WO | WO 01 29220 A3 | 4/2001 |
| WO | WO0190197 | 11/2001 |
| WO | WO 02 22169 | 3/2002 |
| WO | WO 2004/113372 | * 12/2004 |
| WO | 2005053738 A1 | 6/2005 |

OTHER PUBLICATIONS

Drexler et al. Cancer Research, 59, 4955-4963, Oct. 1, 1999.*
Rodeck et al. J Cell Biochem. Oct. 1990; 44 (2): 69-79.*
Sebo et al., Infect. Immun. 63:3851-3857, 1995.*
Osicka et al., Infect. Immun., 68:247-256, 2000.*
Betsou et al, Gene 162: 165-166, 1995.*
Fayolle et al., *J. of Virol.*, vol. 75, No. 16. pp. 7330-7338 (2002).
International Search Report for PCT/EP2004/014086, Mailed Apr. 19, 2005.
Schlect, G. et al., Antigen Targeting to CD11b Allows Efficient Presentation of CD4+ and CD8+ Epitopes and In Vivo Th1-Polarized T Cell Priming, J. Immunol., vol. 173, pp. 6089-6097 (2004.
Guermonprez et al.; "Bordetella Pertussis Adenylate Cyclase Toxin: A Vehicle to Deliver CD8-Positive T-Cell Epitopes into Antigen-Presenting Cells"; Methods in Enzymology, vol. 326, pp. 527-542, (2000).
Renkvist et al.; "A Listing of Human Tumor Antigens Recognized by T Cells"; Cancer Immunology and Immunotherapy, vol. 50, No. 1, pp. 3-15, (2001).
Skipper et al.; "An HLA-A2-Restricted Tyrosinase Antigen on Melanoma Cells Results From Posttranslational Modification and Suggests a Novel Pathway for Processing of Membrane Proteins"; Journal of Experiemntal Medicine, vol. 183, No. 2, pp. 527-534, (1996).
Dadaglio et al.; "Recombant Adenylate Cyclase Toxin of Bordetella Pertussis Induced Cytotoxic T Lymphocyte Responses Against HLA*0201-Restricted Melanoma Epitopes"; International Immunology, vol. 15, No. 12, pp. 1423-1430, (2003).
Jan. 25, 2010 Decision on Appeal in U.S. Appl. No. 10/994,204.
Brichard, et al., The Tyrosinase Gene Codes for an Antigen Recognized by Autologous Cytolytic T Lymphocytes on GLA-A2 Melanomas, J. Exp. Med., Aug. 1, 1993, vol. 178, No. 2, pp. 489-495.

(Continued)

*Primary Examiner* — Oluwatosin Ogunbiyi
(74) *Attorney, Agent, or Firm* — Law Office of Salvatore Arrigo and Scott Lee, LLP

(57) ABSTRACT

An immunogenic composition comprising a recombinant protein comprising a *Bordetella* CyaA, or a fragment thereof, and a peptide that corresponds to a tumor antigen is provided as a cancer treatment. Methods of treatment with this immunogenic composition are also provided. In an embodiment, the therapeutic composition is a treatment for melanoma, and comprises epitopes from the HLA*0201 epitope. These epitopes include Tyr or GnT-V, and are present in the recombinant proteins CyaA-E5-Tyr and CyaA-E5-GnT-V.

5 Claims, 4 Drawing Sheets

(56) References Cited

OTHER PUBLICATIONS

Cryz, et al., Human Immunodeficiency Virus-1 Principal Neutralizing Domain Peptide-Toxin A Conjugate Vaccine, Vaccine, vol. 13, No. 1, pp. 67-71, Jan. 1995.

Fayolle, et al., Therapy of Murine Tumors with Recombinant Bordetella pertussis Adenylate Cyclase Carrying a Cytotoxic T Cell Epitope, J. Immunol. Apr. 1, 1999, vol. 162, No. 7, pp. 4157-4162.

Galye et al., Indentification of Regions in Interleukin-1 Alpha Important for Activity, J. Biol. Chem., vol. 268, No. 29, Issue of Oct. 15, pp. 22105-22111, 1993.

Pietersz et al., Generation of cellular immune responses to antigenic tumor peptides, CMLS, Cell. Mol. Life Sci. 57 (2000) 290-310.

Reilly, et al., Production of Idiotypic and Anti-Idiotypic Antibodies by BALB/c Mice in Response to Immunizations With Glucagon, Fasopressin, or Insulin: Supporting Evidence for the Network Concept, Journal of Immunology, vol. 137, No. 2, pp. 597-602 (1986).

Whisstock et al., Prediction of proteinfunctionfrom protein sequence and structure, Quarterly Reviews of Biophysics 36, 3 (2003), pp. 307-340.

Yang et al., Dendritic Cells Infected with a Vaccinia Vector Carrying the Human gp100 Gene Simultaneously Present Multiple Specificities and Elicit High-Affinity T Cells Reactive to Multiple Epitopes and Restricted by HLA-A2 and -A3, J Immunol 2000; 164:4204-4211.

Preliminary Amendment filed Nov. 21, 2014, in U.S. Appl. No. 14/063,164.

* cited by examiner

RECOMBINANT ADENYLATE CYCLASE TOXIN OF *BORDETELLA* INDUCES T CELL RESPONSES AGAINST TUMORAL ANTIGENS

This is a continuation of application Ser. No. 11/436,757, filed May 19, 2006, now abandoned which is a Continuation of International Application No. PCT/EP2004/014086, filed Nov. 19, 2004, which claims the benefit of U.S. Provisional Application No. 60/523,632, filed Nov. 21, 2003, each of which is incorporated herein by reference in its entirety.

The invention relates to a recombinant adenylate cyclase toxin of *Bordetella* which induces T cell responses against tumoral antigens.

BACKGROUND OF THE INVENTION

This invention relates to compositions and methods for treating cancers.

In many animal tumor models, T cells play an important role in tumor rejection. A variety of tumor antigens recognized by CD4+ or CD8+ tumor reactive T cells have been identified on both murine and human tumors (1). CD8+ cytotoxic lymphocytes (CTL) are of particular interest because these cells specifically recognize tumor cells and kill them. Therefore, an important goal in cancer immunotherapy is to activate tumor-specific CTL.

Study of antigens recognized by CD8+ T cells on human melanoma has identified several MHC-restricted tumor epitopes that correspond to nonmutated or mutated peptides derived from various self proteins (2). Several of these peptides are derived from nonmutated differentiation proteins such as tyrosinase, Melan-A/Mart-1, and gp100. These proteins are specifically expressed in most melanocytes/melanomas, and thus, the HLA-restricted epitopes are presented by most melanoma cells from patients expressing the relevant HLA molecules. Therefore, these antigens could be the targets of immunotherapeutic strategies that are based on immunization against tumor epitopes.

Other antigens expressed on tumor cells have also been described, for example, a peptide derived from an intron sequence of the gene that codes for N-acetylglucosaminyltransferase V (GnT-V) (3). This intron is specifically expressed in melanoma cells and is present in about 50% of melanoma cells.

Various vaccination protocols designed to induce specific anti-tumor CTL responses against these epitopes have been developed, including protocols that use free peptide in IFA (4), recombinant viral vectors (5-7), or dendritic cells (8-11). The application of these approaches to human vaccination remains limited due to potential toxicity of adjuvants, bias towards the response against vector-derived epitopic peptide, or because they are "labor-demanding" (in vitro manipulated DC).

Previously, recombinant plasmids have been used for the expression of *Bordetella* sp. adenylate cyclase (cyaA) and a heterologous DNA inserted in a permissive site of CyaA. These plasmids and resulting recombinant proteins have been useful for inducing immune responses. The immune responses elicited have been in CD8+ T lymphocytes with class I major histocompatibility complexes, as well as in CD4+ T lymphocytes with class II major histocompatibility complexes. (See U.S. Pat. Nos. 5,503,829, 5,679,784, and 5,935,580.) More specifically, the recombinant proteins can be delivered to CD11b expressing cells, such as dendritic cells. (See European Patent Application EP1 188 446 A1, "Proteinaceous vectors for molecule delivery to CD11b expressing cells", and WO/2122169 A2 "Vectors for Molecule Delivery to CD11b Expressing Cells", corresponding to U.S. Pat. No. 387,486, and European Patent Application No. 03291486.3, "Modified *Bordetella* Adenylate Cyclase Comprising or Lacking CD11b/CD18 Interaction Domain and Uses thereof".) See also, El-Azami-El-Idrissi, et al., 2003, Interaction of *Bordetella pertussis* Adenylate Cyclase with CD11b/CD18, J. Biol. Chem., vol. 278, pp. 38514-21.

There exists a need in the art for new antitumor treatments that allow for specific targeting to immune cells and T cell responses. These new strategies should result in specific amplification of immune responses against tumoral antigens.

BRIEF SUMMARY OF THE INVENTION

This invention aids in fulfilling the needs in the art by providing recombinant CyaA proteins that induce immune responses. These responses can be directed towards tumoral antigens.

The invention provides novel methods of treating and immunomonitoring cancers.

The invention provides an immunogenic composition comprising a recombinant protein, wherein the recombinant protein comprises a *Bordetella* adenylate cyclase (CyaA) and a peptide that corresponds to a tumor antigen.

An embodiment of the invention is a method of treating a patient with cancer comprising (1) administering an immunogenic composition to the patient, wherein the immunogenic composition comprises a recombinant protein, wherein the recombinant protein comprises a *Bordetella* CyaA or a specific fragment thereof, and a peptide that corresponds to a tumor antigen, and (2) inducing an immune response, such as a T cell response, in the patient.

An embodiment of the invention is a method of treating a patient with cancer comprising (1) administering an immunogenic composition to the patient, wherein the immunogenic composition comprises a vector expressing a recombinant protein, wherein the recombinant protein comprises *Bordetella* CyaA or a specific fragment thereof, and a peptide that corresponds to a tumor antigen, and (2) inducing a T cell response in the patient.

The T cell response is a CTL response or a T helper response or a CTL and a T helper response.

In an embodiment of the invention, the tumor is a melanoma.

In another embodiment of the invention, the tumor antigen is an HLA*0201 epitope.

Encompassed in the invention is the recombinant protein is CyaA-E5-Tyr or CyaA-E5-GnT-V.

In a further embodiment of the invention, the recombinant protein comprises more than one tumor antigen. In a particular embodiment, at least one tumor antigen is different from the other(s).

The tumor antigen is localized to any permissive site of CyaA.

In an embodiment of the invention CyaA is from *Bordetella pertussis, Bordetella parapertussis*, or *Bordetella bronchiseptica*. In a preferred embodiment CyaA is from *Bordetella pertussis*.

The invention also provides for an immunogenic composition comprising a recombinant protein, wherein the recombinant protein comprises at least one specific fragment of the adenylate cyclase protein that is recognized as a ligand on human and animal cells, and at least one epitope specific for a tumoral antigen. In the recombinant protein of the immunogenic composition CyaA and the tumoral antigen can either be genetically fused or chemically bound (PCT/EPO1/11315).

Furthermore, the invention provides a recombinant protein wherein the recombinant protein comprises *Bordetella* CyaA, or a specific fragment thereof, and a peptide that corresponds to an antigen comprising the GnTV epitope. The antigen is either fused or chemically bound to the CyaA protein or a specific fragment thereof.

The invention also provides a nucleic acid sequence coding for a fusion protein comprising *Bordetella* CyaA, or a specific fragment thereof, and a peptide that corresponds to an antigen comprising the GnTV epitope. In a particular embodiment, said sequence is included in the plasmid deposited at C.N.C.M., Paris, France, on Oct. 16, 2003 under accession number I-3111.

Also included in the invention is a vector expressing a recombinant protein which comprises *Bordetella* CyaA, or a specific fragment thereof, and a peptide that corresponds to an antigen comprising the GnTV epitope. In a particular embodiment, said vector has been deposited at C.N.C.M., Paris, France, on Oct. 16, 2003 under accession number I-3111.

The invention further encompasses a host cell that expresses a recombinant protein comprising *Bordetella* CyaA, or a specific fragment thereof, and a peptide that corresponds to an antigen comprising the GnTV epitope. In a particular embodiment, the host cell expresses the vector that has been deposited at C.N.C.M., Paris, France, on Oct. 16, 2003 under accession number I-3111.

The invention also provides a nucleic acid sequence coding for a fusion protein comprising *Bordetella* CyaA, or a specific fragment thereof, and a peptide that corresponds to an antigen comprising the Tyr epitope. In a particular embodiment, said sequence is included in the plasmid deposited at C.N.C.M., Paris, France, on May 31, 2001 under accession number I-2679.

Another embodiment of the invention is a vector expressing a recombinant protein that comprises *Bordetella* CyaA, or a specific fragment thereof, and a peptide that corresponds to an antigen comprising the Tyr epitope. In a particular embodiment, said vector has been deposited at C.N.C.M., Paris, France, on May 31, 2001, under accession number I-2679.

The invention further encompasses a host cell that expresses a recombinant protein comprising *Bordetella* CyaA, or a specific fragment thereof, and a peptide that corresponds to an antigen comprising the pTyr epitope. In a particular embodiment, the host cell expresses the vector that has been deposited at C.N.C.M., Paris, France, on May 31, 2001, under accession number I-2679.

DESCRIPTION OF THE DRAWINGS

This invention will be described with reference to the drawings in which.

DETAILED DESCRIPTION OF THE PREFERRED EMBODIMENTS

Figure 1:
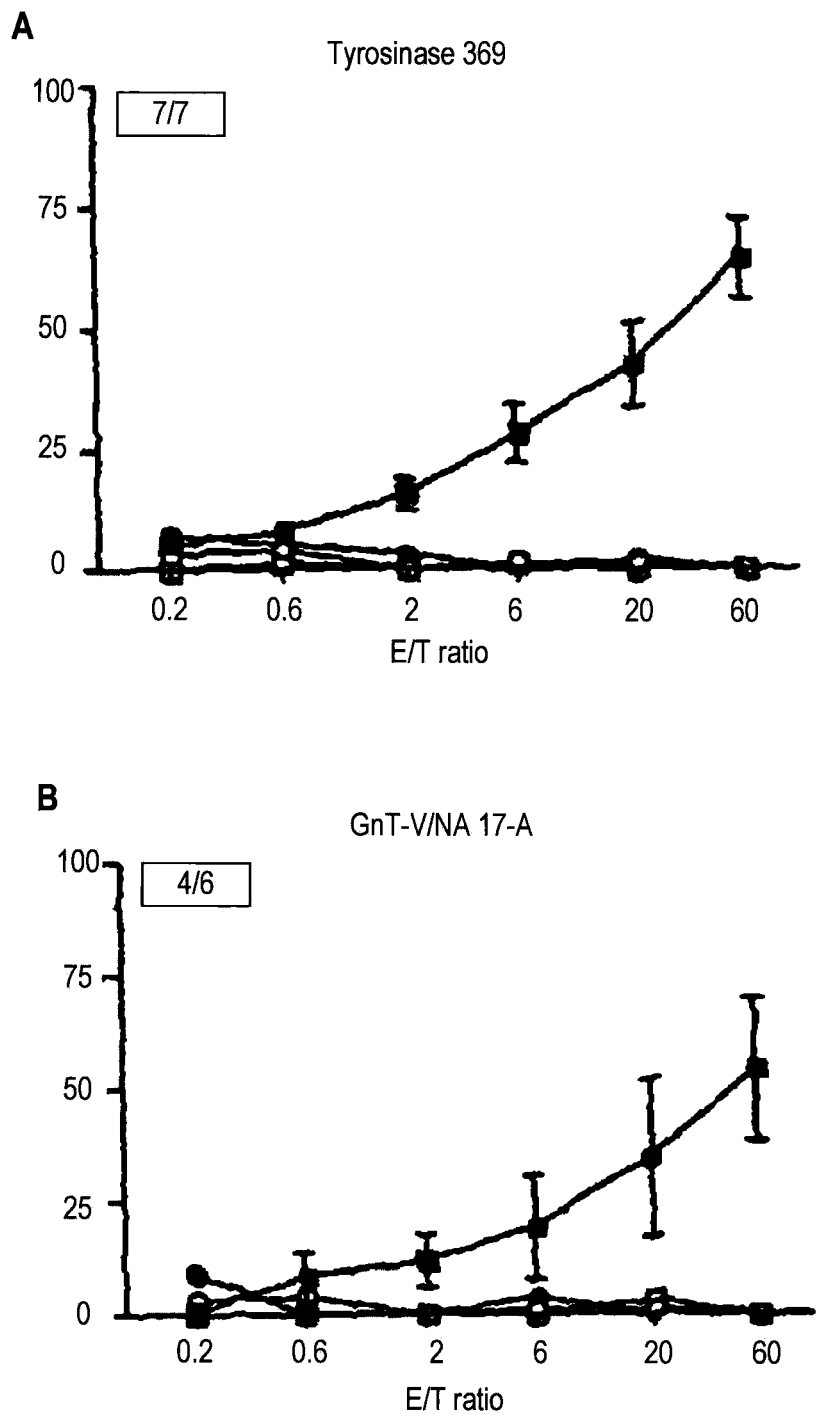
FIG. 1 depicts in vivo induction of CTL responses by recombinant CyaA carrying HLA*0201 restricted melanoma epitopes. HHD-mice received i.p. injections on days 0, 21 and 42 of either 50 µg control CyaA toxin (●, ○) or recombinant CyaA toxins carrying melanoma epitopes (■, □) (A, CyaA-Tyr; B, CyaA-GnT-V) in the presence of 1 mg alum. Seven days after the last injection, spleen cells from immune mice were stimulated in vitro with the priming peptide pTyr (A), or pGnT-V (B) in the presence of irradiated syngenic spleen cells. The cytotoxic activity of these effector cells was measured on $^{51}$Cr-labeled RMA-S-HHD target cells pulsed with the respective peptide (●, ■) or incubated with medium alone (○, □). The data represent mean values of duplicates (SD<10%). Quadrants represent the number of positive mice versus the number of tested mice, and curves represent mean values±SD of responder mice per group from three experiments.

A new approach for CTL activation has recently been developed based on bacterial toxins capable of delivering antigenic epitopes across the plasma cell membrane into the cytosol, where appropriate processing and interaction with MHC-class I molecules can occur. The adenylate cyclase toxin (CyaA) of *Bordetella pertussis* (Glasser, P., et al. 1988 *Bordetella pertussis* adenylate cyclase: the gene and the protein, *Tokai J. Exp. Clin. Med.*, 13 Supp.: 239) has the capacity to deliver its catalytic domain into the cytosol of eukaryotic cells (12). Delivery of a CD8+ T cell epitope inserted into the catalytic domain of CyaA results in intracellular processing and presentation of the epitope by MHC-class I molecules at the surface of antigen presenting cells (13). Furthermore, CyaA specifically binds to $\alpha_M\beta_2$ integrin (CD11b/CD18) (14), and thus, targets the CD11b+ DC subpopulation, which very efficiently induces primary immune responses (15). Therefore, immunization of mice with a recombinant CyaA toxin bearing a viral epitope leads to the induction of strong CTL responses and to a full protection against a lethal viral challenge (16).

Moreover, CyaA toxins carrying a single CTL epitope can also stimulate efficient protective and therapeutic antitumor immunity in mice (17). Importantly, genetically detoxified CyaA toxoids retain the property to induce protective antiviral or antitumoral immunity (17, 18). Thus, CyaA seems to be a safe and efficient non-replicating vector to induce specific immune responses in mice. However, in the view of elaborating cancer immunotherapy using CyaA, it is of particular importance to demonstrate that human tumoral epitopes inserted into CyaA are efficiently processed and presented in association with human MHC molecules.

In one embodiment of the invention, two recombinant CyaA carrying HLA*0201 restricted melanoma epitopes derived either from tyrosinase or from GnT-V were constructed. The potency of these recombinant CyaA to induce in vivo HLA*0201 restricted CTL responses against the inserted epitopes and the ability to deliver these epitopes to human antigen presenting cells is demonstrated in the Examples below.

It was discovered that CyaA of *Bordetella pertussis* is able to deliver CD8+ T cell epitopes into the cytosol of CD11b+ dendritic cells following its specific interaction with the $\alpha_M\beta_2$ integrin (CD11b/CD18). This delivery results in intracellular processing and presentation by MHC-class I molecules of the CD8+ T cell epitopes inserted into CyaA. Indeed, CyaA toxins carrying a single CTL epitope can induce efficient protective and therapeutic antitumor immunity in mice.

It was further discovered that these recombinant CyaA proteins induce strong anti-melanoma CTL responses in HLA*0201-transgenic mice, even after a single intravenous immunization without adjuvant. The responses are long lasting, being detected as long as five months after the last injection.

Finally, it was discovered that human dendritic cells, treated with the recombinant CyaA, process and efficiently present melanoma epitopes to human CTL clones. The recombinant CyaA proteins of the invention demonstrate that tumoral epitopes inserted into CyaA are efficiently processed and presented in association with human MHC molecules. Therefore, CyaA is capable of activating antitumoral CTL in humans, and is a novel factor for cancer immunotherapy.

As used herein, the term immunogenic composition relates to a composition that leads to an immunological response and that is associated with therapeutic treatments, such as treatments against cancers.

As used herein the terms "*Bordetella* CyaA" or "*Bordetella* adenylate cyclase" encompass the CyaA or a fragment thereof, either modified or not. The modifications can include deletion of some internal amino acids. For example, CyaA may have no catalytic activity, but the specific binding to CD11b/CD18 receptor and the process of translocation of the catalytic domain are not affected. The term "*Bordetella*" refers to the adenylate cyclase protein of a pathogen of *Bordetella* species. Said pathogen can be *Bordetella pertussis, Bordetella parapertussis*, or *Bordetella bronchiseptica*.

As used herein, the term "antigen" or "epitope" refers to a peptide including a protein that can induce an immune response. The term "heterologous" refers to the nature of the antigen bound to the CyaA protein, which induces an immune response different from that of the CyaA protein. A heterologous antigen or epitope can be fused to CyaA or chemically bound to CyaA, for instance.

As used herein, the term immunogenic refers to a characteristic of a protein as being able to elicit an immune response in a mammal, particularly in a human. The term "immune response" refers to many effects that are caused by cells of the immune system, such as, for instance, a CTL response and/or a T helper response, and in the context of the invention includes, but are not limited to, activation of tumor-specific cytotoxic lymphocytes. As used herein, the term "immunotherapy" refers to a therapy for a disease that relies on an immune response.

In addition to the recombinant protein or vector of the invention, the immunogenic composition of the invention can include adjuvants and excipients to allow an increase and modulation in the immune response. These adjuvants are diverse in nature. They can, for example, comprise liposomes, oily phases, for example, the Freund type of adjuvants, which are generally used in the form of an emulsion with an aqueous phase, or, more commonly, can comprise water-insoluble inorganic salts. These inorganic salts can comprise, for example, aluminum hydroxide, zinc sulfate, colloidal iron hydroxide, calcium phosphate, or calcium chloride. Aluminum hydroxide ($Al(OH)_3$) is the most commonly used adjuvant.

The invention also encompasses recombinant proteins comprising *Bordetella* CyaA, or a specific fragment thereof, and the peptide pTyr (YMDGTMSQV). Said peptide may comprise extended flanking sequences. The pTyr peptide corresponds to the melanoma HLA*0201 restricted epitope from the 369-377 region of tyrosinase. Note that the amino acids 369-377 of human tyrosinase are YMNGTMSQV. However, the Asn residue at position 371 (N) of tyrosinase is naturally deamidated to Asp (D) of this epitope in living cell so that the true epitope recognized by the CTL clones in vivo are recognizing sequence YM<u>D</u>GTMSQV.

Furthermore, an epitope with an extended tanking sequence of amino acids:360-385 of human Tyrosinase is SSMHNALHIYMNGTMSQVQGSANDPI (with N371 converted to D), which corresponds to SEQ. ID. NO.: 3.

An epitope derived from the human N-acetylglucosaminyltransferase V gene is VLPDVFIRC (SEQ ID NO: 4) (Y Guilloux, et al. A peptide recognized by human cytolytic T lymphocytes on HLA-A2 melanomas is encoded by an intron sequence of the N-acetylglucosaminyltransferase V gene, J. Exp. Med. 1996 183: 1173-1183.) The Gnt-V epitope is encoded by an intron sequence that may code for a 74 amino acid long polypeptide (*H. sapiens* DNA for exon encoding for N-acetylglucosaminyltransferase V; Accession #X91652). Furthermore, the epitope with extended flanking sequences from human N-acetylglucosaminyltransferase V is MVLPDVFIRCVVFCL (SEQ ID NO: 5).

The invention also encompasses the recombinant fusion protein comprising *Bordetella* CyaA, or a specific fragment thereof, and the peptide pGnT-V (VLPDVFIRC). Said peptide may comprise extended flanking sequences. The peptide pGnT-V corresponds to the HLA*0201 restricted epitope NA17-A derived from an intron of the N-acetylglucosaminyltransferase V gene.

In one preferred embodiment of the invention the recombinant protein is CyaA-Tyr. The term "CyaA-Tyr" means a fusion protein comprising the tyrosinase melanoma epitope of HLA*0201, which can be prepared as described in Example 1, and *Bordetella pertussis* CyaA. The term "CyaA-E5-Tyr" refers to the CyaA-Tyr protein in which the catalytic activity of CyaA has been genetically inactivated. See, for instance, Example 1.

In another preferred embodiment of the invention, the recombinant protein is CyaA-E5-GnT-V. The term "CyaA-E5-GnT-V" means a fusion protein comprising the NA17-A melanoma epitope of HLA*0201 derived from an intron of the N-acetylglucosaminyl-transferase V gene, which can be prepared as described in Example 1, and *Bordetella pertussis* CyaA. The term "CyaA-E5-GnT-V" refers to the Cya-GnT-V protein in which the catalytic activity of CyaA has been genetically inactivated. Once again, see, for instance, Example 1.

In yet another embodiment of the invention, the recombinant protein between CyaA and pTyr or pGnT-V is modified from the structure of CyaA-Tyr, CyaA-GnT-V, CyaA-E5-Tyr, or CyaA-E5-GnT-V. Modification of these embodiments can include the addition of flanking regions, which are sequences of amino acids that surround the peptides comprising the recombinant protein, and were described above. These flanking sequences can enhance processing. Flanking sequences can also be sequences which is not naturally surround the antigen but which specifically enhance the antigen processing by antigen preventing cells.

In yet another embodiment, the recombinant proteins can be modified by including multiple identical heterologous epitopes. For instance, Tyr or GnT-V epitope, as described above, or other melanoma epitopes.

In further embodiments of the invention, the recombinant protein can include at least one specific fragment of the adenylate cyclase protein, such as, but not limited to, CyaA the 373-1706 region or the 1166-1281 region which are recognized as a ligand on human and animal cells, such as, dendritic cells, and at least one epitope specific for a cancer antigen, such as, but not limited to, pTyr or GnT-V.

In another embodiment of the invention, the recombinant protein can include multiple epitopes from one or more tumoral antigens.

Another embodiment of the invention includes permissive sites of CyaA that differ from those provided in the Examples. The antigen portion of the recombinant protein used in the tests of the invention can be localized to any permissive site of the CyaA adenylate cyclase protein WO 93/21324. In addition, the invention encompasses tests and immunogenic compositions that utilize only fragments of the CyaA adenylate cyclase in the recombinant protein (see EPO 03/291486.3).

As used herein, the term "permissive site" relates to a site where the heterologous peptide can be inserted without substantially affecting the desired functional properties of the adenylate cyclase toxin, i.e. without affecting the domains necessary for the specific binding to CD11b/CD18 receptor and advantageously without affecting the process of translocation of the catalytic domain.

Permissive sites of the *Bordetella pertussis* adenylate cyclase include, but are not limited to, residues 137-138 (Val-Ala), residues 224-225 (Arg-Ala), residues 228229 (Glu-Ala), residues 235-236 (Arg-Glu), and residues 317-318 (Ser-Ala) (see Sebo et al., 1985). The following additional permissive sites are also included in embodiments of the invention: residues 107-108 (Gly-His), residues 132-133 (Met-Ala), residues 232-233 (Gly-Leu), and 335-336 (Gly-Gln) and 336-337. (See generally, Glaser et al., 1988 *Bordetella pertussis* adenylate cyclase: the gene and the protein, *Tokai J. Exp. Clin. Med.*, 13 Suppl.: 239-52.)

As used herein, the terms "specific region of the adenylate cyclase protein" or "fragment of the CyaA adenylate cyclase" relates to a fragment of said protein including the protein wherein some amino acids which are not on the tumoral parts of the protein have been deleted, and the desired functional properties of adenylate cyclase toxin are not substantially affected, i.e. the domains necessary for the specific binding to CD11b/CD18 receptor and the process of translocation of the catalytic domain are not affected.

The terms "tumor antigen" or "cancer antigen" refer to any substance from a tumor that elicits an immune response and reacts specifically with antibodies or T cells. Said substance can be from any origin, either spontaneous or from a virus, which transforms cells to form a tumor. Examples of such viruses are HHV8, HCV, and HBV. The antigen or epitope must be present on the surface of the tumor cell.

As used herein, the term "a peptide that corresponds to an antigen" encompass an antigen, an epitope, or an antigen or an epitope flanked by naturally or non-naturally occurring flanking regions, which specifically enhance antigen processing by antigen presenting cells.

The term "epitope" refers to the minimal peptide sequence of an antigen that can induce an immune response.

The term "peptide" refers to a series of amino acids linked by amide bonds, comprising at least 3 amino acids, and preferably at least 6 amino acids.

The immunogenic composition of the invention can be used in solution, for example, but not limited to, in PBS, or with adjuvants, for example, but not limited to alum. The immunogenic composition can be administered intramuscularly, subcutaneously, intravenously, or intradermally. The immunogenic composition can be administered in amounts from 0.5-10 mg, preferably 1-5 mg, 1.5-3 mg, or more preferably 1.50 mg. The effects of these treatments can be monitored by assaying the levels of IFN-γ with ELISPOT, ELISA, or CTL activation assays, or other appropriate immunoassays.

Publications illustrate the use of recombinant adenylate cyclase of *Bordetella* sp. for diagnosis and immunomonitoring, i.e., Vordermeier H. Martin et al (Infection and Immunity, November 2004, p. 6255-2261) and Schlecht G, et al (The Journal of Immunology 2004, p. 6089-6097).

The adenylate cyclase of *Bordetella* Sp. represents a new delivery system able to specifically stimulate CD8$^+$ T lymphocytes leading to protective antiviral and antitumoral immunity in mice (16, 17). CyaA is a powerful non-replicating vector for induction of adaptive immunity and is useful in vaccines. Demonstration, according to this invention, that the inserted epitopes can be processed and presented in association with human MHC molecules is an indispensable prerequisite for the use of this vector in humans.

By using recombinant CyaA in which human melanoma epitopes expressing the human HLA*0201 class I molecule were present, strong and lasting melanoma specific CTL responses could be induced in HLA transgenic mice. Similar results were obtained with recombinant detoxified CyaA devoid of adenylate cyclase activity. CyaA represents an efficient vector to induce specific CTL responses in vivo because more than 80% of immunized HHD mice responded to the tyrosinase epitope inserted into CyaA following one i.v. injection without adjuvant, while only 26% of HHD mice respond to this epitope following one injection of 100 μg of peptide in the presence of IFA (partially in 26). In addition, it was surprisingly observed according to this invention that human DC efficiently processed these recombinant molecules for antigenic peptide presentation to human CTL. Strikingly, the recombinant CyaA-Tyr was much more efficient than the synthetic peptide in delivering the tyrosinase epitope to DC.

Alternative antigen delivery systems based on recombinant viruses usually result in an in vitro presentation efficiency that is lower than the synthetic peptide. The surprising results from in vivo and in vitro experiments according to the invention underline the power of CyaA as delivery system, and show that CTL responses can be obtained in humans after immunization with recombinant CyaA and thus, that efficient immunotherapy can be achieved with this vector. However, the immunogenicities of the two recombinant CyaA tested in this study were quite different. Indeed, strong CTL responses in HHD mice were induced with only one i.p. injection of CyaA-Tyr in the absence of adjuvant, while three i.p. injections of CyaA-GnT-V, in the presence of alum, were required to generate specific CTL responses. The weak efficiency of CyaA-GnT-V to deliver GnT-V melanoma epitope was also evidenced in vitro, since human DC incubated with this vector poorly stimulated an anti-GnT-V CTL clone as compared to CyaA-Tyr, which efficiently stimulated a specific anti-tyrosinase CTL clone.

This difference can be explained by the fact that the GnT-V peptide grafted into CyaA-GnT-V was poorly processed, as compared to the tyrosinase peptide inserted into CyaA-Tyr. Indeed, flanking regions of a given epitope are known to influence the proteolytic generation of the mature peptide (27-29) and particularly for subdominant and/or cryptic epitopes (30). Therefore, it is expected that modification of the molecular context of GnT-V epitope into CyaA can enhance the efficiency of processing of this epitope by APC. On the contrary, the sequence flanking the tyrosinase epitope in CyaA-Tyr appears to allow its efficient processing.

Furthermore, CyaA-Tyr is very efficient in activating HLA*0201-restricted CD8+ T cell in vivo, because a single intravenous immunization or two i.p. injections without adjuvant were sufficient to generate strong specific CTL responses. This is explained by the fact that CyaA targets specifically CD11b+ DC, the most potent APC to induce primary response, as a result of its interaction with the $\alpha_M\beta_2$ integrin expressed by these cells (14). Thus, CyaA has the exceptional property of specifically delivering antigens to the cytosolic Ag class I presentation pathway of professional APC.

Further improvements of the CyaA recombinant strategy are also possible. First, multiple insertions of CD8+ T cell epitopes into the same recombinant molecule has already been successfully achieved. Indeed, immunization of mice with recombinant CyaA carrying three different epitopes, including a LCMV epitope, leads to the induction of specific CTL responses for each of the three epitopes, as well as protection against a lethal LCMV challenge (31). Detoxified CyaA carrying multiple melanoma epitopes constitute a good alternative to induce multispecific CTL responses. Furthermore, additional insertion of CD4+ T cell epitopic peptides is also possible. Although the implication of CD8+ T cells in eradication of established tumors has been clearly demonstrated (32), T helper cells can also be required to induce efficient anti-tumoral responses (33-35). Recombinant CyaA can also deliver epitopes into the MHC class II processing pathway (36) and is able to induce, in vivo, both specific Th1 and CTL responses (37). This characteristic is of great interest for vaccination strategies where both kinds of T cell responses have to be induced, noticeably in the context of cancer immunotherapy.

Plasmid pTRACE5-GnTV is a derivative of the expression vector pTRACG that expresses the cyaC and cyaA genes from *Bordetella pertussis* under the control of the phage Pr promoter (pTRCAG also harbors an ampicillin resistance selectable marker and the thermosensitive λ repressor $CI^{857}$). In pTRACE5-GnTV, the cyaA gene is modified by insertion of a dipeptide Leu-Gln between codons 188 and 189 of wild-type CyaA (resulting in the inactivation of the adenylate cyclase activity) and by insertion of a DNA sequence encoding the following peptide sequence PASVLPDVFIRCGT (SEQ ID NO: 6) inserted between codons 224 and 240 of CyaA. The peptide sequence VLPDVFIRC (SEQ. ID. NO.: 4), which is contained within SEQ ID NO 6, corresponds to the HLA-A2 restricted melanoma epitope NA17-A derived from the N-acetylglucosaminyl-transferase V gene. (G. Dadaglio, et al. (2003) Recombinant adenylate cyclase of *Bordetella pertussis* induces CTL responses against HLA-A2-restricted melanoma epitope. Int. Immuno.) Plasmid XL1/pTRACE5-GnTV was deposited at C.N.C.M. on Oct. 16, 2003, with accession number I-3111.

Plasmid pTRACE-5-Tyros369 is a derivative of the expression vector pTRACG that expresses the cyaC and cyaA genes from *Bordetella pertussis* under the control of the λ phage Pr promoter (pTRCAG also harbors an ampicillin resistance selectable marker and the thermosensitive λ repressor $CI^{857}$). In pTRACE5-Tyros369, the cyaA gene is modified by insertion of a dipeptide Leu-Gln between codons 188 and 189 of wild-type CyaA (resulting in the inactivation of the adenylate cydase activity) and by insertion of a DNA sequence encoding the following peptide sequence PASYMDGTM-SQVGTRARLK (SEQ ID NO: 7) inserted between codons 204; and 240 of CyaA. The peptide sequence YMDGTMSQV (SEQ ID NO: 2), which is contained within SEQ ID NO: 7, corresponds to the amino acid sequence 369-377 of tyrosinase. Plasmid XL1/pTRACE5-Tyros369 was deposited at C.N.C.M. on May 31, 2001, with accession number I-2679.

The abbreviations used are as follows: CTL: cytotoxic T lymphocytes; DC: dendritic cells; PBMC: peripheral blood mononuclear cells; CyaA: adenylate cyclase of *Bordetella* sp; Tyr: tyrosinase; GnT-V: N-acetylglucosaminyl-transferase V; GM-CSF: granulocyte-macrophage colony-stimulating factor; IFN: interferon; i.p.: intraperitoneal; i.v.: intravenous.

This invention will be described in greater detail in the following Examples.

Example 1

Materials and Methods

Mice.

HHD mice are H-2D$^{-/-}$ β2m$^{-/-}$ double knock out mice expressing the HHD transgene comprising the α1 (H) and α2 (H) domains of HLA*0201 linked to α3 transmembrane and cytoplasmic domains of H-2 D$^b$ (D), with the α1 domain linked to human β2-microglobulin. Thus, the only MHC class I molecule expressed by the HHD mice is the modified HLA*0201 molecule (19). HHD mice were bred and housed in animal facilities of Institut Pasteur.

Peptides.

synthetic peptides pTyr (YMDGTMSQV), which corresponds to SEQ ID NO: 2 and to the melanoma HLA*0201 restricted epitope from the 369-377 region of tyrosinase (20, 21), and pGnT-V (VLPDVFIRC), which corresponds to SEQ ID NO: 4 and to the HLA*0201 restricted epitope NA17-A derived from an intron of the N-acetylglucosaminyl-transferase V gene (3) were purchased from Neosystem (Strasbourg, France).

Construction of recombinant *Bordetella pertussis* adenylate cyclase toxins and toxoids carrying melanoma epitopes. The recombinant CyaA toxin, CyaA Tyr, harbors a 14 amino acid long polypeptide sequence corresponding to SEQ ID NO: 8 (PASYMDGTMSQVGT, one-letter code for amino acid) genetically inserted between residues 224 and 225 of CyaA. This sequence contains a single copy of the HLA*0201 restricted melanoma epitope derived from tyrosinase (amino acid 369-377, underlined sequence above). Recombinant CyaA toxin CyaA-GnT-V harbors a 14 amino acid long (PASVLPDVFIRCGT)insert, which corresponds to SEQ ID NO: 6, at the same position and contains a single copy of the HLA*0201 restricted melanoma epitope NA17-A derived from the N-acetylglucosaminy-transferase V gene, which corresponds to SEQ ID NO: 4.

These recombinant toxins were produced in the *E. coli* strain BLR (Novagen) by using expression vectors that are derivatives of the pTRACG plasmid (22), modified by the insertion between the NheI and KpnI restriction sites of appropriate synthetic double stranded oligonucleotides encoding the indicated polypeptide sequences. The *E. coli* strain XL1-Blue (Stratagene) was used for all DNA manipulations that were done according to standard protocols. The recombinant proteins were purified to homogeneity from inclusion bodies by a two-step procedure that includes DEAE-Sepharose and Phenyl-Sepharose chromatographies, as described previously (23).

The recombinant toxins CyaA-Tyr and CyaA-GnT-V are enzymatically active and therefore cytotoxic. The recombinant toxoids CyaA-E5-Tyr and CyaA-E5-GnT-V are enzymatically inactive, detoxified variants of CyaA-Tyr and CyaA-GnT-V respectively. They are unable to synthesize CAMP as a result of a dipeptide insertion within a critical region of the catalytic site (23). CyaA-E5-Tyr and CyaA-E5-GnT-V toxoids were produced in *E. coli* by using expression vectors that are derivatives of the pTRACE5 plasmid: this plasmid was obtained by insertion of the hexanucleotide CTGCAG in an EcoRV site located in the 5' part of the cyaA DNA sequence. This results in an in-frame insertion of the dipeptide Leu-Gln between Asp188 and Ile 189 of CyaA (23). The same synthetic double stranded oligonucleotides described above were inserted between the NheI and KpnI sites of pTRACE5 to create plasmids pTRAC-E5-Tyr and pTRAC-E5-GnT-V. The recombinant CyaA-E5-Tyr and CyaA-E5-GnT-V toxoids were purified to homogeneity as described (23).

All purified recombinant toxins and toxoids were more than 90% pure as judged by SDS-gel analysis. The toxin concentrations were determined spectrophotometrically from the absorption at 280 nm using a molecular extinction coefficient of 142,000 $M^{-1}$ $cm^{-1}$.

Oligonucleotide synthesis and DNA sequencing were performed by Genaxis (France). Cultures in fermentors were performed by the Service des Fermentations facility from Institut Pasteur.

Mouse Immunization.

Six to ten week old female HHD mice were immunized with two or three i.p. injections at 21 day intervals of either 50 μg CyaA or recombinant CyaA carrying melanoma epitopes in the presence or in the absence of 1 mg alum. In some experiments, mice were immunized with one i.v. injection of 50 μg of the recombinant CyaA in PBS. Detoxified recombinant CyaA-E5 were used in the same conditions. Spleens were surgically removed seven days after the last injection, except for the analysis of long lasting responses, where spleens were removed three or five months after the last injection.

In Vitro Cytotoxic Assay.

Spleen cells from immunized mice were stimulated in vitro with 10 μg/ml of pTyr or pGnT-V peptides corresponding to the priming epitope in the presence of syngeneic irradiated naive spleen cells in complete medium (RPMI 1640 medium containing L-Alanyl-L-Glutamine dipeptide supplemented with 10% fetal calf serum, $5\times10^{-5}$ M 2-mercaptoethanol, 100 U/ml penicillin, 100 μg/ml streptomycin and 20 mM Hepes) for five days. The cytotoxic activity of these effector cells was tested in a 4-h $^{51}$Cr-release assay on HHD transfected $TAP^{-/-}$ RMA-S cells (RMA-S-HHD) loaded with the relevant peptides as target cells. $^{51}$Cr-labeling was performed as follows: one day before the cytotoxic test, RMA-S-HHD cells were incubated overnight at room temperature in 7% $CO_2$ equilibrated RPMI 1640 medium supplemented with 20 mM Hepes. Then, cells were incubated 3 h at room temperature with or without 20 μg/ml of the relevant peptide, washed once and radiolabeled with 100 μCi of $^{51}$Cr for 1 h at 37° C.

Various effectors to target ratios were used and all assays were done in duplicate. The radioactivity released in the supernatant of each well was measured. The percentage of specific lysis was calculated as 100×(experimental release−spontaneous release)/(maximum release−spontaneous release). Maximum release was generated by adding 10% triton X-100 to target cells and spontaneous release was obtained with target cells incubated in medium alone. Mice are considered to be responders when at least 20% specific lysis was observed at the highest E/T ratio. The results are expressed as mean values±SD of responder mice per group. No specific CTL activity was obtained with splenocytes from immunized mice stimulated in vitro with an irrelevant peptides.

Human Dendritic Cells.

Human dendritic cells were derived from adherent monocytes as follows: Peripheral blood mononuclear cells were isolated from buffy coats obtained from the HLA*0201 hemochromatosis patient LB2050 by centrifugation on Leucosep tubes (Greiner, Frickenhausen, Germany) previously centrifuged 30 sec at 2200 rpm with 15 ml of Lymphoprep (Nycomed Pharma, Oslo, Norway). These tubes were centrifuged at 2200 rpm for 20 min at room temperature and the top part containing plasma was discarded. The interphase containing the PBMC was harvested and washed at least three times in cold phosphate buffer with 1 mM EDTA in order to eliminate the remaining platelets. The PBMC were then left to adhere for 1 h in culture flasks at a density of $2\times10^6$ cells/$cm^2$ in RPMI 1640 supplemented with amino-acids (L-arginine 116 μg/ml, L-asparagine 36 μg/ml, L-glutamine 216 μg/ml), antibiotics, and 10% fetal calf serum (hereafter referred as culture medium). Non-adherent cells were discarded, adherent cells were washed twice carefully with 20 ml of medium and incubated in culture medium with 200 U/ml human IL-4 and 70 ng/ml human GM-CSF. On day two and four, 5 ml of medium were removed and 10 ml containing 700 ng of GM-CSF were added. IL-4 was also supplemented at 200 U/ml for the total volume of the flask. The cells were used between day five and seven.

Human CTL Clones.

CTL clone IVS-B directed against the HLA*0201 restricted Tyr epitope (positions 369-377) of tyrosinase was previously described (24). The clone was stimulated weekly with 50 U/ml human IL-2, irradiated HLA*0201 transfected MZ2-MEL melanoma cells pulsed with 2 μg/ml pTyr peptide, and irradiated LG2-EBV cells as feeder cells. The CTL clone CMU 579 613 specific for the HLA*0201 restricted epitope derived from GnT-V was obtained from the blood of a healthy donor following a recently described method (25). Briefly, the PBMC were stimulated for two weeks with the antigenic peptide pGnT-V, human IL-2, IL-4, and IL-7. On day 13, PBMC were stained with an HLA*0201 tetramer folded with the pGnT-V peptide. Tetramer positive lymphocytes were cloned using flow cytometry. They were stimulated for two weeks with irradiated allogeneic HLA*0201-positive EBV-transformed B cells pulsed with the peptide, irradiated allogeneic PBL, IL-2, IL-4, and IL-7, and then maintained by weekly stimulation with irradiated HLA*0201-positive peptide-pulsed allogeneic tumor cells and irradiated allogeneic EBV-B cells. Both CTL clones were maintained in Iscove's medium supplemented with 10% of human serum, amino acids, and antibiotics.

In Vitro Stimulation Assay of Human CTL Clones.

For the stimulation assay, 10,000 immature dendritic cells were seeded in U-bottom microplates in 25 µl of X-Vivo 10 medium (Whittaker Bioproducts, Walkersville, USA). 25 µl of CyaA preparations diluted in X-Vivo 10 medium at different concentrations were added to the wells. After 30 min of incubation, the corresponding CTL clones were incubated with these cells (75 µl of X-vivo medium containing 104 anti-tyrosinase CTL clone IVS-B or $10^4$ anti-GnT-V CTL clone CMU 579 6/3) and IL-2 (at a final concentration of 25 U/ml). The supernatants were collected after 20 h and their IFN-γ content was determined by ELISA (Biosource International, Camarillo, Calif.). To control the ability of DC incubated with the various detoxified recombinant toxoids to stimulate the CTL clones, they were exogenously loaded with the relevant antigenic peptides, incubated with the relevant CTL clones and the production of IFN-γ was similarly assessed (data not shown).

Example 2

Induction of Melanoma-Specific CTL Responses by Immunization of HHD Transgenic Mice with Recombinant CyaA Carrying HLA*0201-Restricted Melanoma Epitopes To determine whether the CyaA toxin is capable of inducing specific CTL responses against human tumoral antigens, two recombinant CyaA carrying HLA*0201-restricted human melanoma epitopes were constructed. The first recombinant CyaA expresses the epitope 369-377 from the tyrosinase antigen (CyaA-Tyr) and the second one expresses the epitope NA17-A derived from an intron of the N-acetylglucosaminyl-transferase V (CyaA-GnT-V). The ability of recombinant CyaA to induce CTL responses against these two epitopes in vivo was assessed in HHD mice, which are transgenic for the human MHC class I molecule HLA*0201 and have been shown to develop HLA*0201-restricted CTL responses against tumoral peptides (26). HHD mice were immunized by 3 i.p. injections of 50 µg of recombinant CyaA with alum. After in vitro stimulation of splenocytes with the corresponding peptide, CTL responses were tested in a chromium release assay, using as targets peptide-pulsed RMA-S-HHD cells, which express the same transgene as HHD mice. As shown in FIG. 1, both recombinant toxins carrying either Tyr or GnT-V epitopes induce strong CTL responses against target cells loaded with the relevant peptide. These CTL responses were antigen-specific since only peptide sensitized target cells were killed and CTL activity was not detected on target cells loaded with irrelevant peptides (data not shown). As expected, no significant CTL responses were observed in mice immunized with the wild type CyaA showing that the induction of specific CTL responses required in vivo priming by the epitope inserted into recombinant CyaA.

Figure 2:
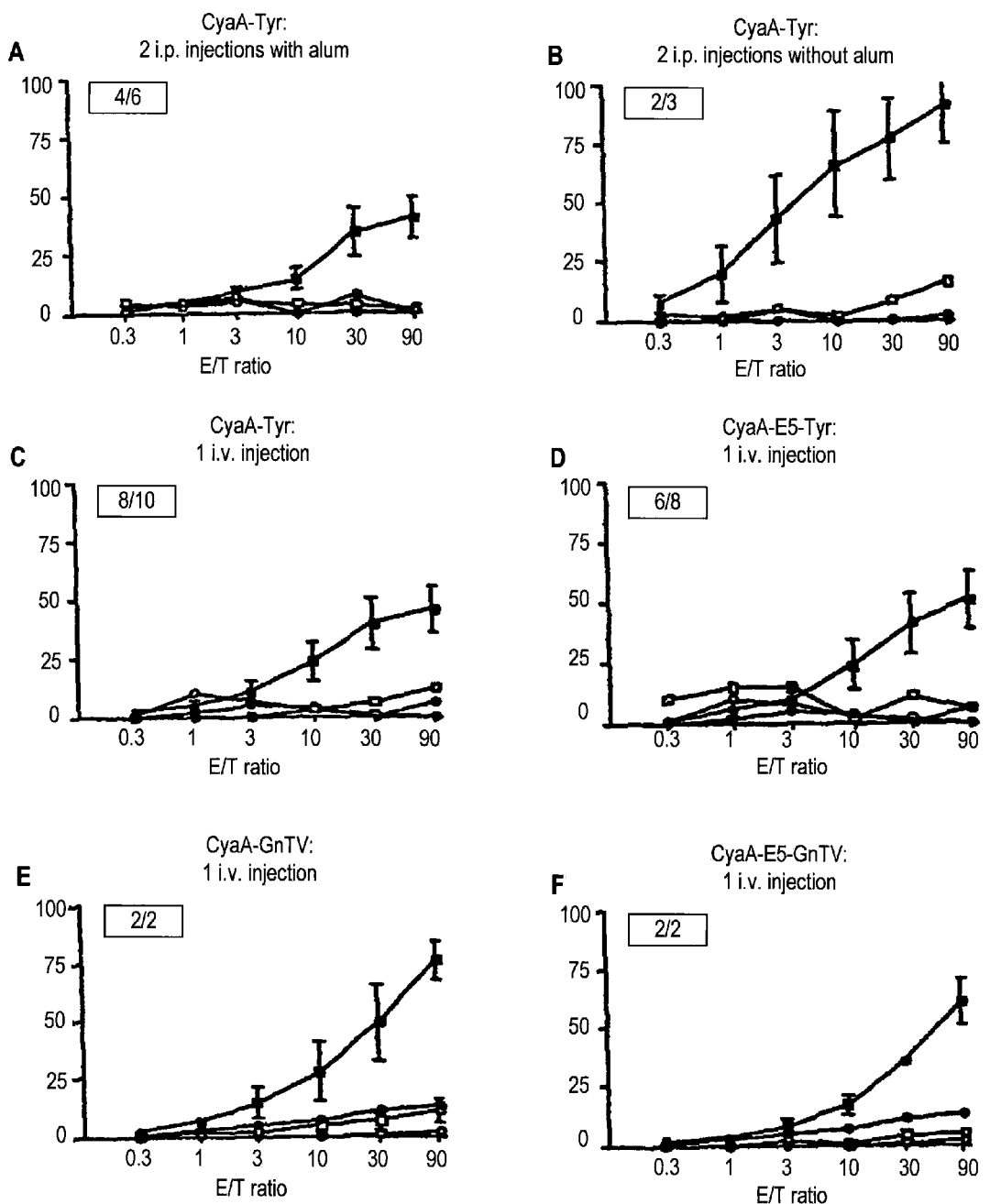
FIG. 2 depicts induction of melanoma-specific CTL responses by recombinant CyaA carrying melanoma epitopes using different routes of immunization. Panels A and B: HHD mice were immunized i.p. twice on days 0 and 21 with 50 µg wild-type CyaA (●, ○) or recombinant CyaA-Tyr (■, □) in the presence (A) or in the absence of 1 mg alum (B). Panels C and E: HHD mice were immunized by one i.v. injection with 50 µg control wild type CyaA (●, ○) or recombinant CyaA-Tyr (■, □) (C) or recombinant CyaA-GnT-V (■, □) (E) in the absence of adjuvant. Panels D and F: HHD mice were immunized by one i.v. injection with 50 µg control detoxified CyaA-E5 (●, ○) or detoxified recombinant CyaA-E5-Tyr (■, □) (D) or recombinant CyaA-E5-GnTV (■, □) (F) in the absence of adjuvant. Seven days after the last injection, spleen cells from immune mice were stimulated in vitro with priming peptides in the presence of irradiated syngeneic spleen cells. The cytotoxic activity was measured on $^{51}$Cr-labeled RMA-S-HHD target cells pulsed with the priming peptide (●, ■) or incubated with medium alone (○, □). The results show cumulative data from 24 experiments. Quadrants represent the number of positive mice versus the number of tested mice, and curves represent mean values±SD of responder mice per group. The results obtained after immunization with toxic and detoxified CyaA are not statistically different using a t test.

Induction of CTL responses by CyaA-Tyr was then analyzed using different immunization protocols with or without alum as adjuvant. As illustrated in FIGS. 2A and B, two i.p. injections of CyaA-Tyr were enough to induce specific CTL responses against the tyrosinase epitope, even in the absence of alum. Induction of strong specific CTL responses was also observed following a single injection of 50 µg of CyaA-Tyr without adjuvant using the i.v. route (FIG. 2C). As expected, these CTL responses were observed only when using peptide pulsed target cells and splenocytes from mice immunized with the recombinant CyaA-Tyr, showing the specificity of the responses. These results demonstrate the high efficiency of CyaA-Tyr to induce specific CTL responses against the tyrosinase melanoma epitope. However, using similar conditions of immunization (2 or 1 i.p. injections with or without alum), no specific CTL response was observed with the recombinant toxin CyaA-GnT-V, indicating that this toxin is less efficient to generate specific CTL response than the CyaA-Tyr (data not shown). However, by the intravenous route, one injection of CyaA-GnT-V was sufficient to induce a strong CTL response (FIG. 2E).

Finally, CTL responses induced by genetically detoxified mutants of CyaA carrying Tyrosinase or GnTV epitopes that are devoid of adenylate cyclase activity following insertion of a dipeptide into the catalytic site were analyzed. HHD mice immunized with these detoxified molecules developed specific CTL responses against both tyrosinase and GnTV epitopes (FIGS. 2D, 2F), which were comparable to the responses of mice immunized with the toxic forms of CyaA carrying the corresponding epitope. These results indicate that HLA*0201-restricted. CTL induction is independent of the catalytic activity as it was clearly demonstrated for a viral epitope from LCMV in BALB/C mice (18).

Example 3

Recombinant CyaA-Tyr Induces Long Lasting Memory CTL Responses

Figure 3:
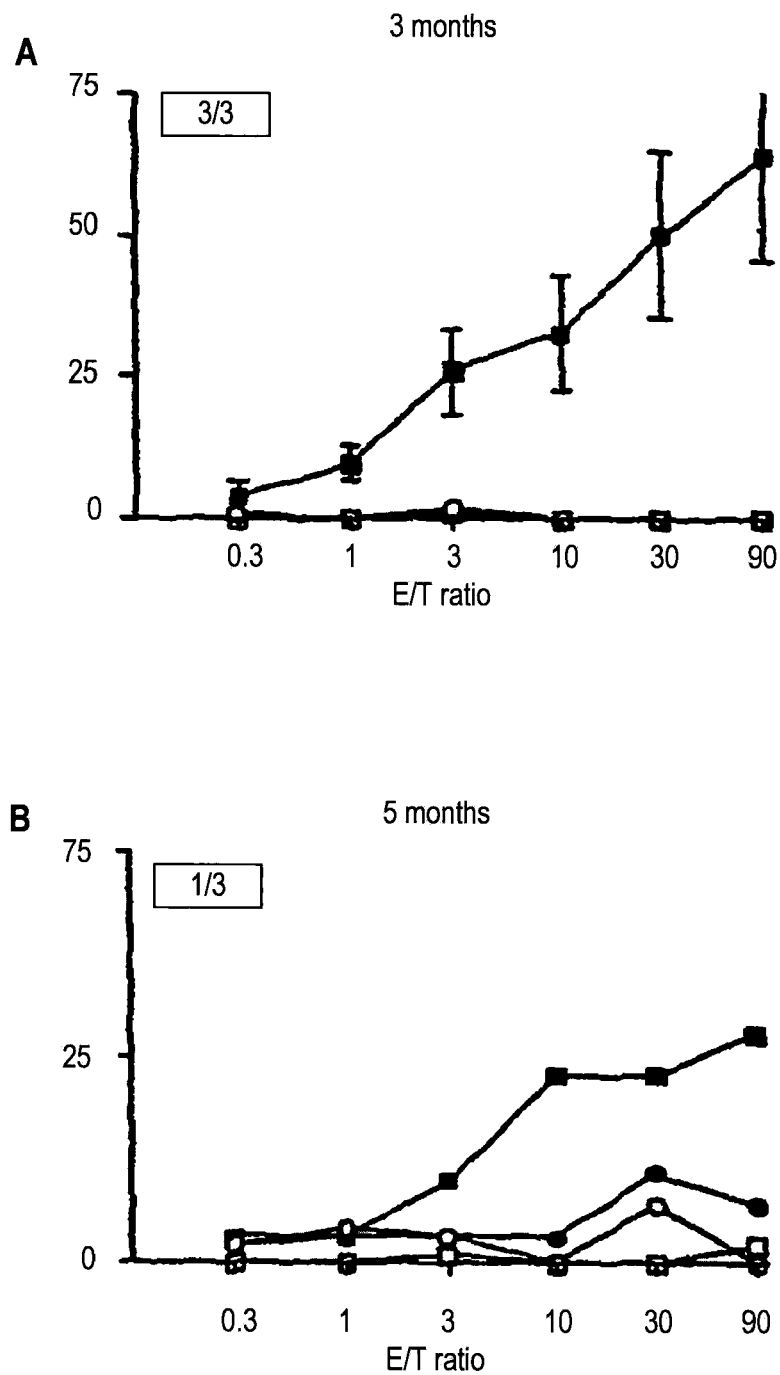
FIG. 3 demonstrates that immunization of mice with CyaA-Tyr induces a long-lasting specific memory CTL activity. HHD mice were immunized i.p. twice on days 0 and 21 with 50 µg wild-type CyaA (●, ○) or recombinant CyaA-Tyr (■, □) in the presence of 1 mg alum. Three months (A) or five months (B) after the last injection, spleens were removed and specific CTL activity was measured after in vitro stimulation as described in FIG. 1 on $^{51}$Cr-labeled RMA-S-HHD target cells pulsed with the peptide pTyr (●, ■) or incubated with medium alone (○, □). Quadrants represent the number of positive mice versus the number of tested mice. Curves represent mean values±SD of responder mice per group from one experiment.

To analyze the persistence of the CTL responses induced by the recombinant CyaA bearing melanoma epitope, HHD mice received two i.p. injections of 50 µg of CyaA-Tyr in the presence of alum. Three and five months after the last injection, splenocytes from immunized mice were stimulated in vitro over five days with the peptide pTyr and then, their cytolytic activity was tested against peptide pulsed RMA-S-HHD target cells. As illustrated in FIG. 3, CyaA-Tyr induced a long-lasting specific CTL response because specific cytotoxic activity could be detected in all mice three months after the last injection, and even after five months in one animal.

Example 4

HLA*0201-Restricted Peptides Inserted into CyaA are Processed and Presented by HLA*0201+ Human DC In vivo induction of specific CTL responses by recombinant CyaA indicates that inserted epitopes are efficiently processed and presented by murine APC. However, it is important to demonstrate that human APC are also able to process and present these HLA*0201-restricted epitopes inserted into CyaA. Because DC are the most important APC to induce primary T cell responses, the ability of HLA*0201+ DC incubated with the recombinant CyaA to stimulate human CTL clones specific for the epitopes inserted into the recombinant CyaA was determined. For these experiments, human DC were generated in vitro from HLA*0201+ adherent PBMC in the presence of GM-CSF and IL-4. Increasing doses of CyaA-E5-Tyr. CyaA-E5-GnT-V or control CyaA-E5 were then added and presentation of the antigenic peptides was assessed by measuring the ability of the treated DC to stimulate the relevant CTL in an IFN-γ production assay.

Figure 4:
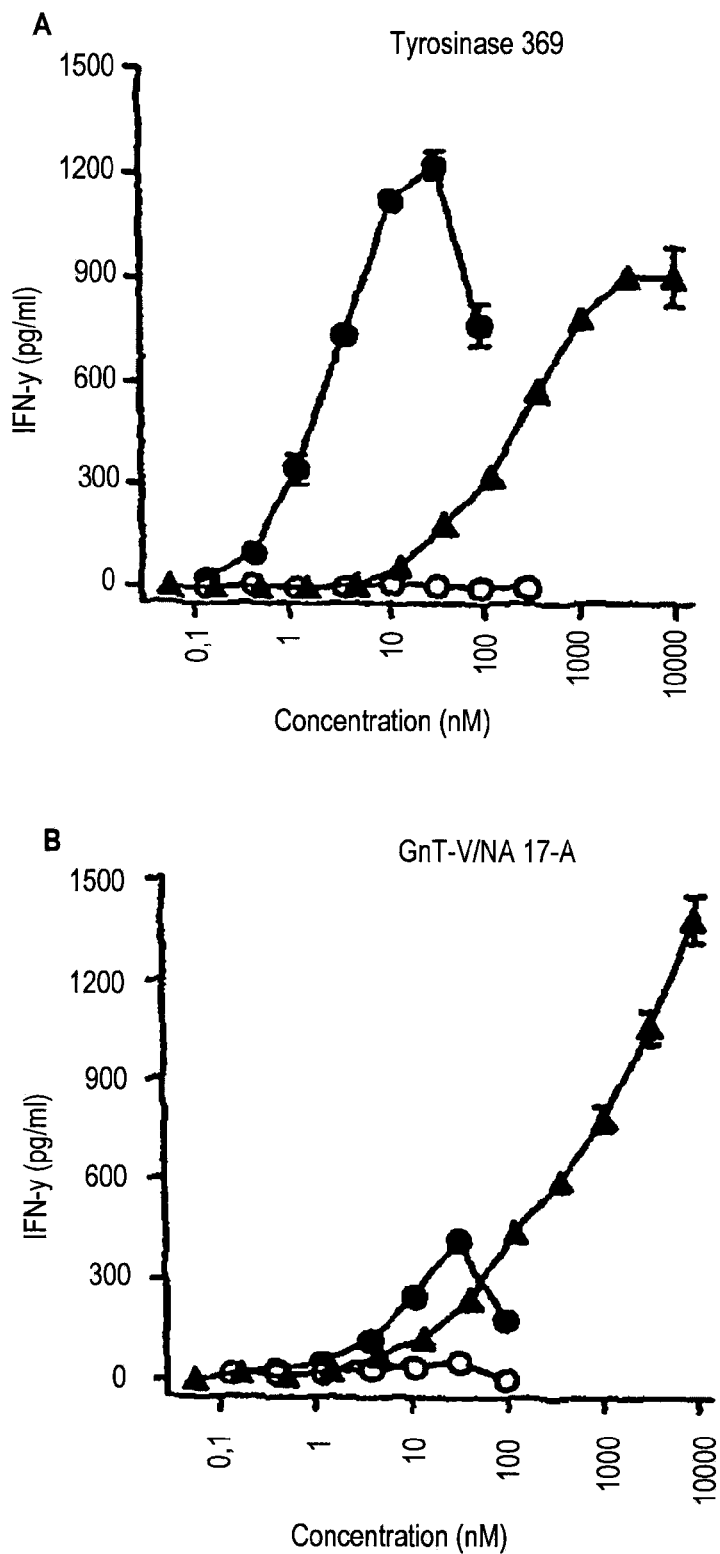
FIG. 4 depicts stimulation of human specific CTL clones by human dendritic (DC) cells incubated with recombinant CyaA-E5-Tyr or CyaA-E5-GnT-V. Due to the cytotoxicity of CyaA, only detoxified recombinant CyaA were tested in vitro. Immature HLA*0201+ DC derived from human monocytes were incubated with CyaA-E5 (○), recombinant CyaA-E5-Tyr (●) (A), CyaA-E5-GnT-V (●) (B) or with the relevant antigenic peptide (▲), and were used as APC (Antigen Presenting Cells) to stimulate anti-tyrosinase CTL clone IVS-B (A) or anti-GnT-V CTL clone CMU 579 6/3 (B). The secretion of IFN-γ by the CTL clones was assessed by ELISA. The results are expressed as the mean concentration of IFN-γ released in the supernatants from duplicate wells and are representative of three independent experiments. Standard errors of the mean are indicated.

As shown in FIG. 4A, human DC incubated with CyaA-E5-Tyr induced a high production of IFN-γ by the tyrosinase-specific CTL clone, indicating that the tyrosinase epitope is efficiently processed and presented in association with HLA*0201 molecules. The specificity of this recognition was confirmed by the lack of stimulation of two irrelevant CTL clones (data not shown) and by the lack of stimulation of the tyrosinase-specific clone by DC treated with the control toxoid CyaA-E5 (FIG. 4A). Presentation of the tyrosinase epitope was proportional to the dose of CyaA-Tyr up to 30 nM. Under these conditions, higher doses appeared to be toxic for the DC, as indicated by the low recognition of the treated DC and by their decreased ability to present the synthetic peptide loaded exogenously (data not shown).

In order to assess the relative efficiency of antigen presentation using CyaA as delivery system a titration curve of the tyrosinase synthetic peptide, which was pulsed on similar DC, was also performed. As shown on FIG. 4A, the CyaA-Tyr was up to 100 times more efficient than the synthetic peptide to induce the presentation of the epitope by DC.

Human DC incubated with CyaA-E5-GnT-V induced a weak but reproducible production of IFN-γ by the GnT-V specific CTL clone, as compared with DC incubated with the peptide pGnT-V (FIG. 4B). This result indicates that human DC are able to present the GnT-V epitope inserted into CyaA, although with a moderate efficiency.

In summary, these results clearly demonstrate the capacity of human DC to process and present human epitopes inserted into CyaA.

Example 5

CyaA Toxin Constructions which do not Induce a Response

CyaA-Mel 21, which comprises the epitope gp100-280, and includes the inserted sequence YLEPGTVTA formed the GP 100 melanoma-associated tumor antigen, does not include a CTL response. Similarly, CyaA-CEA 13, which comprises the epitope CEA 571-579, and has the inserted sequence YLSGANLNL from the Carcinoma Embryonic Antigen, does not induce a CTL response. Neither of these toxins induce a CTL response specific for the inserted epitopes in the HHD mouse. Furthermore, some human dendritic cells cannot present the inserted epitope CyaA-Mel 21 (epitope gp100-280) to a human CTL clone. Therefore, this toxin is probably also ineffective in humans. These two toxins, CyaA-Mel21 and CyaA-CEA13, are identical to CyaA-Tyr and CyaA-GnTV, but differ only in the inserted sequences. Therefore, only the epitopes are different, and so the response to CyaA-Tyr and CyaA-GNTV are epitope specific.

Finally, the Cya-Mage toxin, which comprises the Mage A10/A2 epitope with the inserted sequence GLYDGMEHL from the melanoma protein Mage 10, induces very good CTL response in HHD mouse, but is inefficient in humans under the protocol described above. Therefore, a positive response in the mouse is not always indicative of a positive response in humans. In general, human responses are epitope and species specific.

REFERENCES

The following references are cited herein. The entire disclosure of each reference is relied upon and incorporated by reference herein.

1. Van Pel, A., van der Bruggen, P., Coulie, P. G., Brichard, V. G., Lethe, B., van den Eynde, B., Uyttenhove, C., Renauld, J. C., and Boon, T. 1995. Genes coding for tumor antigens recognized by cytolytic T lymphocytes. *Immunol Rev* 145: 229.
2. Kawakami, Y. and Rosenberg, S. A. 1997. Human tumor antigens recognized by T-cells. *Immunol Res* 16:313.
3. Guilloux, Y., Lucas, S., Brichard, V. G., Van Pel, A., Viret, C., De Plaen, E., Brasseur, F., Lethe, B., Jotereau, F., and Boon, T. 1996. A peptide recognized by human cytolytic T lymphocytes on HLA-A2 melanomas is encoded by an intron sequence of the N-acetylglucosaminyltransferase V gene. *J Exp Med* 183:1173.
4. Rosenberg, S. A., Yang, J. C., Schwartzentruber, D. J., Hwu, P., Marincola, F. M., Topalian, S. L., Restifo, N. P., Dudley, M. E., Schwarz, S. L., Spiess, P. J., Wunderlich, J. R., Parkhurst, M. R., Kawakami, Y., Seipp, C. A., Einhom, J. H., and White, D. E. 1998. Immunologic and therapeutic evaluation of a synthetic peptide vaccine for the treatment of patients with metastatic melanoma. *Nat Med* 4:321.
5. Valmori, D., Levy, F., Miconnet, I., Zajac, P., Spagnoli, G. C., Rimoldi, D., Lienard, D., Cerundolo, V., Cerottini, J. C., and Romero, P. 2000. Induction of potent antitumor CTL responses by recombinant vaccinia encoding a melan-A peptide analogue. *J Immunol* 164:1125.
6. Wang, M., Bronte, V., Chen, P. W., Gritz, L., Panicali, D., Rosenberg, S. A., and Restifo, N. P. 1995. Active immunotherapy of cancer with a nonreplicating recombinant fowlpox virus encoding a model tumor-associated antigen. *J Immunol* 154:4685.
7. Zhai, Y., Yang, J. C., Kawakami, Y., Spiess, P., Wadsworth, S. C., Cardoza, L. M., Couture, L. A., Smith, A. E., and Rosenberg, S. A. 1996. Antigen-specific tumor vaccines. Development and characterization of recombinant adenoviruses encoding MART1 or gp100 for cancer therapy. *J Immunol* 156:700.
8. Mayordomo, J. I., Zorina, T., Storkus, W. J., Zitvogel, L., Celluzzi, C., Falo, L. D., Melief, C. J., Ildstad, S. T., Kast, W. M., and Deleo, A. B. 1995. Bone marrow-derived dendritic cells pulsed with synthetic tumour peptides elicit protective and therapeutic antitumour immunity. *Nat Med* 1:1297.
9. Nestle, F. O., Alijagic, S., Gilliet, M., Sun, Y., Grabbe, S., Dummer, R., Burg, G., and Schadendorf, D. 1998. Vaccination of melanoma patients with peptide- or tumor lysate-pulsed dendritic cells. *Nat Med* 4:328.
10. Toes, R. E., van der Voort, E. I., Schoenberger, S. P., Drijfhout, J. W., van Bloois, L., Storm, G., Kast, W. M., Offringa, R., and Melief, C. J. 1998. Enhancement of tumor outgrowth through CTL tolerization after peptide vaccination is avoided by peptide presentation on dendritic cells. *J Immunol* 160:4449.
11. Yang, S., Kittlesen, D., Slingluff, C. L., Jr., Vervaert, C. E., Seigler, H. F., and Darrow, T. L. 2000. Dendritic cells infected with a vaccinia vector carrying the human gp100 gene simultaneously present multiple specificities and elicit high-affinity T cells reactive to multiple epitopes and restricted by HLA-A2 and -A3. *J Immunol* 164:4204.
12. Ladant, D. and Ullmann, A. 1999. *Bordetella pertussis* adenylate cyclase: a toxin with multiple talents. *Trends in Microbiology* 7:172.

13. Guermonprez, P., Ladant, D., Karimova, G., Ullmann, A., and Leclerc, C. 1999. Direct delivery of the *Bordetella pertussis* adenylate cyclase toxin to the MHC class I antigen presentation pathway. *J Immunol* 162:1910.
14. Guermonprez, P., Khelef, N., Blouin, E., Rieu, P., Ricciardi-Castagnoli, P., Guiso, N., Ladant, D., and Leclerc, C. 2001. The adenylate cyclase toxin of *Bordetella pertussis* binds to target cells via the alpha(M)beta(2) integrin (CD11b/CD18). *J Exp Med* 193:1035.
15. Banchereau, J., Briere, F., Caux, C., Davoust, J., Lebecque, S., Liu, Y. J., Pulendran, B., and Palucka, K. 2000. Immunobiology of dendritic cells. *Annu Rev Immunol* 18:767.
16. Saron, M. F., Fayolle, C., Sebo, P., Ladant, D., Ullmann, A., and Leclerc, C. 1997. Anti-viral protection conferred by recombinant adenylate cyclase toxins from *Bordetella pertussis* carrying a CD8+ T cell epitope from lymphocytic choriomeningitis virus. *Proc Natl Acad Sci USA* 94:3314.
17. Fayolle, C., Ladant, D., Karimova, G., Ullmann, A., and Leclerc, C. 1999. Therapy of murine tumor with recombinant *Bordetella pertussis* adenylate cyclase carrying a cytotoxic T cell epitope. *J. Immunol.* 162:4157.
18. Fayolle, C., Sebo, P., Ladant, D., Ullmann, A., and Leclerc, C. 1996. In vivo induction of CTL responses by recombinant adenylate cyclase of *Bordetella pertussis* carrying viral CD8+ T cell epitopes. *J. Immunol* 156:4697.
19. Pascolo, S., Bervas, N., Ure, J. M., Smith, A. G., Lemonnier, F. A., and Peramau, B. 1997. HLA-A2.1-restricted education and cytolytic activity of CD8(+) T lymphocytes from beta2 microglobulin (beta2m) HLA-A2.1 monochain transgenic H-2Db beta2m double knockout mice. *J Exp Med* 185:2043.
20. Wolfel, T., Van Pel, A., Brichard, V., Schneider, J., Seliger, B., Meyer zum Buschenfelde, K. H., and Boon, T. 1994. Two tyrosinase nonapeptides recognized on HLA-A2 melanomas by autologous cytolytic T lymphocytes. *Eur J Immunol* 24:759.
21. Skipper, J. C., Hendrickson, R. C., Gulden, P. H., Brichard, V., Van Pel, A., Chen, Y., Shabanowitz, J., Wolfel, T., Slingluff, C. L., Jr., Boon, T., Hunt, D. F., and Engelhard, V. H. 1996. An HLA-A2-restricted tyrosinase antigen on melanoma cells results from posttranslational modification and suggests a novel pathway for processing of membrane proteins. *J Exp Med* 183:527.
22. Gmira, S., Karimova, G., and Ladant, D. 2001. Characterization of recombinant *Bordetella pertussis* adenylate cyclase toxins carrying passenger proteins. *Res Microbiol* 152:889.
23. Guermonprez, P., Fayolle, C., Karimova, G., Ullmann, A., Leclerc, C., and Ladant, D. 2000. *Bordetella pertussis* adenylate cyclase toxin: a vehicle to deliver CD8+ T-cell epitopes into antigen-presenting cells. *Methods Enzymol* 326:527.
24. Brichard, V., Van Pel, A., Wolfel, T., Wolfel, C., De Plaen, E., Lethe, B., Coulie, P., and Boon, T. 1993. The tyrosinase gene codes for an antigen recognized by autologous cytolytic T lymphocytes on HLA-A2 melanomas. *J Exp Med* 178:489.
25. Coulie, P. G., Karanikas, V., Colau, D., Lurquin, C., Landry, C., Marchand, M., Dorval, T., Brichard, V., and Boon, T. 2001. A monoclonal cytolytic T-lymphocyte response observed in a melanoma patient vaccinated with a tumor-specific antigenic peptide encoded by gene MAGE-3. *Proc Natl Acad Sci USA* 98:10290.
26. Firat, H., Garcia-Pons, F., Tourdot, S., Pascolo, S., Scardino, A., Garcia, Z., Michel, M. L., Jack, R. W., Jung, G., Kosmatopoulos, K., Mateo, L., Suhrbier, A., Lemonnier, F. A., and Langlade-Demoyen, P. 1999. H-2 class I knockout, HLA-A2.1-transgenic mice: a versatile animal model for preclinical evaluation of antitumor immunotherapeutic strategies. *Eur J Immunol* 29:3112.
27. Del Val, M., Schlicht, H. J., Ruppert, T., Reddehase, M. J., and Koszinowski, U. H. 1991. Efficient processing of an antigenic sequence for presentation by MHC class I molecules depends on its neighboring residues in the protein. *Cell* 66:1145.
28. Gileadi, U., Gallimore, A., Van der Bruggen, P., and Cerundolo, V. 1999. Effect of epitope flanking residues on the presentation of N-terminal cytotoxic T lymphocyte epitopes. *Eur J Immunol* 29:2213.
29. Velders, M. P., Weijzen, S., Eiben, G. L., Elmishad, A. G., Kloetzel, P. M., Higgins, T., Ciccarelli, R. B., Evans, M., Man, S., Smith, L., and Kast, W. M. 2001. Defined flanking spacers and enhanced proteolysis is essential for eradication of established tumors by an epitope string DNA vaccine. *J Immunol* 166:5366.
30. Mo, A. X., van Lelyveld, S. F., Craiu, A., and Rock, K. L. 2000. Sequences that flank subdominant and cryptic epitopes influence the proteolytic generation of MHC class I-presented peptides. *J Immunol* 164:4003.
31. Fayolle, C., Osickova, A., Osicka, R., Henry, T., Rojas, M. J., Saron, M. F., Sebo, P., and Leclerc, C. 2001. Delivery of multiple epitopes by recombinant detoxified adenylate ayclase of *Bordetella pertussis* induces protective antiviral immunity. *J Virol* 75:7330.
32. Hanson, H. L., Donermeyer, D. L., Ikeda, H., White, J. M., Shankaran, V., Old, L. J., Shiku, H., Schreiber, R. D., and Allen, P. M. 2000. Eradication of established tumors by CD8+ T cell adoptive immunotherapy. *Immunity* 13:265.
33. Kem, D. E., Klamet, J. P., Jensen, M. C., and Greenberg, P. D. 1986. Requirement for recognition of class II molecules and processed tumor antigen for optimal generation of syngeneic tumor-specific class I-restricted CTL. *J Immunol* 136:4303.
34. Toes, R. E., Ossendorp, F., Offring a, R., and Melief, C. J. 1999. CD4+ T cells and their role in antitumor immune responses. *J Exp Med* 189:753.
35. Schnell, S., Young, J. W., Houghton, A. N., and Sadelain, M. 2000. Retrovirally transduced mouse dendritic cells require CD4+ T cell help to elicit antitumor immunity: implications for the clinical use of dendritic cells. *J Immunol* 164:1243.
36. Loucka, J., Schlecht, G., Vodolanova, J., Leclerc, C., and ebo, P. 2002. Delivery of a MalE CD4(+)-T-cell epitope into the major histocompatibility complex class II antigen presentation pathway by *Bordetella pertussis* adenylate cyclase. *Infect Immun* 70:1002.
37. Dadaglio, G., Moukrim, Z., Lo-Man, R., Sheshko, V., Sebo, P., and Leclerc, C. 2000. Induction of a polarized Th1 response by insertion of multiple copies of a viral T-cell epitope into adenylate cyclase of *Bordetella pertussis*. *Infect Immun* 68:3867.
38. Vordermeier H. et al, November 2004, Recognition of Mycobacterial Antigens Delivered by Genetically Detoxified *Bordetella pertussis* Adenylate Cyclase by T cells from Cattle with Bovine Tuberculosis. Infection and Immunity, p. 6255-6261.
39. Schlecht G. et al, 2004, Targeting to CDIIb allows efficient presentation of CD4+ and CD8+ T cell epitopes and in vivo Th 1 polarized T cell priming.
40. Dadaglio G. et al, 2003, "Recombinant adenylate cyclase toxin of *Bordetella pertussis* induces cytotoxic T lymphocyte responses against HLA*0201-restricted melanoma epitopes", International Immunology, vol. 15, No. 12, pp. 1423-1430.

What is claimed is:

1. An immunogenic composition comprising a recombinant protein, wherein the recombinant protein comprises:

a *Bordetella pertussis* adenylate cyclase (*B. pertussis* CyaA), or a fragment thereof, comprising the domains necessary for the specific binding to the CD11b/CD18 receptor and the process of translocation of the catalytic domain, said domains being not affected in said fragment; and a polypeptide sequence consisting of PASVLPDVFIRCGT (SEQ ID NO: 6) inserted into a permissive site of the CyaA;

wherein intravenous immunization of HHD mice with the immunogenic composition induces a cytotoxic T lymphocyte (CTL) response specific for the epitope VLPDVFIRC (SEQ ID NO: 4); and wherein human dendritic cells incubated with the immunogenic composition induce in vitro a specific cytotoxic T lymphocyte (CTL) response by human CTL clones specific for the epitope VLPDVFIRC (SEQ ID NO: 4) when the CTL clones are incubated with the human dendritic cells.

2. The immunogenic composition as claimed in claim 1, wherein the *B. pertussis* CyaA, or a fragment thereof, is detoxified or devoid of catalytic activity.

3. The immunogenic composition as claimed in claim 2, wherein the recombinant protein is CyaA-E5-GnT-V.

4. An immunogenic composition comprising a recombinant protein, wherein the recombinant protein comprises a *Bordetella pertussis* adenylate cyclase (*B. pertussis* CyaA); and a polypeptide sequence consisting of PASVLPDVFIRCGT (SEQ ID NO: 6) inserted into a permissive site of the CyaA;

wherein intravenous immunization of HHD mice with the immunogenic composition induces a cytotoxic T lymphocyte (CTL) response specific for the epitope VLPDVFIRC (SEQ ID NO: 4); and wherein human dendritic cells incubated with the immunogenic composition induce in vitro a specific cytotoxic T lymphocyte (CTL) response by human CTL clones specific for the epitope VLPDVFIRC (SEQ ID NO: 4) when the CTL clones are incubated with the human dendritic cells.

5. The immunogenic composition as claimed in claim 1, wherein the recombinant protein is encoded by the plasm id XL1/pTRACE5-GnT-V deposited at CNCM on Oct. 16, 2003, with Accession Number 1-3111.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 1

Tyr Met Asp Gly Thr Met Ser Gln Val
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 2

Tyr Met Asn Gly Thr Met Ser Gln Val
 1               5

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: peptide

<400> SEQUENCE: 3

Ser Ser Met His Asn Ala Leu His Ile Tyr Met Asn Gly Thr Met Ser
 1               5                  10                  15

Gln Val Gln Gly Ser Ala Asn Asp Pro Ile
             20                  25

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 4

Val Leu Pro Asp Val Phe Ile Arg Cys
 1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: peptide

<400> SEQUENCE: 5

Met Val Leu Pro Asp Val Phe Ile Arg Cys Val Val Phe Cys Leu
 1               5                  10                  15

<210> SEQ ID NO 6
<211> LENGTH: 14
<212> TYPE: PRT

```
<213> ORGANISM: Artificial Sequence
<220> FEATURE:
<223> OTHER INFORMATION: Description of Artificial Sequence: peptide

<400> SEQUENCE: 6

Pro Ala Ser Val Leu Pro Asp Val Phe Ile Arg Cys Gly Thr
 1               5                  10

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: peptide

<400> SEQUENCE: 7

Pro Ala Ser Tyr Met Asp Gly Thr Met Ser Gln Val Gly Thr Arg Ala
 1               5                  10                  15

Arg Leu Lys

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: peptide

<400> SEQUENCE: 8

Pro Ala Ser Tyr Met Asp Gly Thr Met Ser Gln Val Gly Thr
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 9

Tyr Leu Glu Pro Gly Thr Val Thr Ala
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 10

Tyr Leu Ser Gly Ala Asn Leu Asn Leu
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: peptide

<400> SEQUENCE: 11

Gly Leu Tyr Asp Gly Met Glu His Leu
 1               5
```